(12) United States Patent
Hyoudou et al.

(10) Patent No.: US 8,289,529 B2
(45) Date of Patent: Oct. 16, 2012

(54) ANALYZING APPARATUS

(75) Inventors: Masatake Hyoudou, Ehime (JP);
Takuya Suzuki, Ehime (JP)

(73) Assignee: Panasonic Corporation, Osaka (JP)

( * ) Notice: Subject to any disclaimer, the term of this patent is extended or adjusted under 35 U.S.C. 154(b) by 251 days.

(21) Appl. No.: 12/863,914

(22) PCT Filed: Jan. 15, 2009

(86) PCT No.: PCT/JP2009/000120
§ 371 (c)(1),
(2), (4) Date: Jul. 21, 2010

(87) PCT Pub. No.: WO2009/093422
PCT Pub. Date: Jul. 30, 2009

(65) Prior Publication Data
US 2010/0309487 A1    Dec. 9, 2010

(30) Foreign Application Priority Data

Jan. 21, 2008  (JP) ................................ 2008-009951
Nov. 19, 2008  (JP) ................................ 2008-295002

(51) Int. Cl.
*G01B 11/14* (2006.01)
(52) U.S. Cl. ....................................... 356/620; 356/614
(58) Field of Classification Search ........... 356/601–620
See application file for complete search history.

(56) References Cited

U.S. PATENT DOCUMENTS

| | | | |
|---|---|---|---|
| 3,771,878 A | 11/1973 | Molloy et al. | |
| 6,992,278 B2* | 1/2006 | Sjoberg et al. | 250/231.17 |
| 7,295,320 B2* | 11/2007 | Ostlin et al. | 356/445 |
| 2002/0097632 A1* | 7/2002 | Kellogg et al. | 366/220 |
| 2003/0054563 A1* | 3/2003 | Ljungstrom et al. | 436/172 |
| 2004/0264323 A1* | 12/2004 | Worthington et al. | 369/47.27 |
| 2005/0169611 A1 | 8/2005 | Wakita et al. | |
| 2005/0185569 A1* | 8/2005 | Coombs et al. | 369/275.4 |
| 2007/0264722 A1* | 11/2007 | Coombs et al. | 436/164 |
| 2008/0019875 A1 | 1/2008 | Shiga | |
| 2009/0021741 A1* | 1/2009 | Kim et al. | 356/440 |

FOREIGN PATENT DOCUMENTS

| | | |
|---|---|---|
| JP | 7-500910 | 1/1995 |
| JP | 2003-270128 | 9/2003 |
| JP | 2006-284409 | 10/2006 |
| WO | 93/08893 | 5/1993 |
| WO | 2006/011393 | 2/2006 |

OTHER PUBLICATIONS

International Search Report of PCT/JP2009/000120, dated Mar. 3, 2009.

* cited by examiner

*Primary Examiner* — Michael P Stafira
(74) *Attorney, Agent, or Firm* — Hamre, Schumann, Mueller & Larson, P.C.

(57) ABSTRACT

An analyzing device 1 includes position detection marks 18, each having one of a reflective surface, a refractive surface, and a light shielding surface that block output light incident on a sensor 113 from a light source 12 when the output light reaches a rotation detection position just before or behind measurement spots 17a, 17b, and 17c of the analyzing device 1. Output signals from the sensor 113 for reading the measurement spots 17a, 17b, and 17c are stored in a memory 28, the positions of the measurement spots 17a, 17b, and 17c are determined based on light receiving data stored in the memory 28, and only a desired analyzing signal is extracted. Thus even when the number of measurement spots increases, it is possible to read the measurement spots without adding any components.

2 Claims, 12 Drawing Sheets

ANALYZING APPARATUS

TECHNICAL FIELD

The present invention relates to an analyzing apparatus for transferring an analyzing device, which contains a sample liquid collected from an organism and the like, to a measurement spot by a centrifugal force and analyzing the sample liquid.

BACKGROUND ART

In the prior art, a liquid collected from an organism and the like is analyzed by a known analyzing method using an analyzing device having fluid channels formed therein. The analyzing device can control a fluid with a rotator. By using a centrifugal force, the analyzing device can dilute a sample liquid, measure a solution, separate a solid component, transfer and distribute a separated fluid, and mix a solution and a reagent, thereby enabling various biochemical analyses.

Patent Document 1 describes an analyzing device 50 for transferring a solution by a centrifugal force. As shown in FIG. 14, the analyzing device 50 is configured such that a sample liquid as a specimen is injected into a measuring chamber 52 from an inlet 51 by an inserting instrument such as a pipette, the sample liquid is retained by the capillary force of the measuring chamber 52, and then the sample liquid is transferred to a separating chamber 53 by a rotation of the analyzing device. Such an analyzing device using a centrifugal force as a power source for transferring a liquid is preferably shaped like a disk, so that microchannels for controlling the transfer of the liquid can be radially arranged without causing any excessive area.

The sample liquid and a diluent are mixed and agitated by accelerating or decelerating a turntable, on which the analyzing device 50 is set, in the same rotation direction, or rotating the turntable in forward and reverse directions. Further, a measurement position detector made up of a light source and a light receiving part accesses a mixed solution of the sample liquid transferred to a measurement spot and a diluent and reads an analyzing signal.

Moreover, the timing of arrival at a measurement position is decided based on detection by a rotary encoder attached to the turntable and a signal obtained by detecting a trigger mark provided on the analyzing device. At this point, the light source is turned on and light from the light source is read by the light receiving part.

Patent Document 1: National Publication of International Patent Application No. 7-500910

DISCLOSURE OF THE INVENTION

Problem to be Solved by the Invention

In this case, three sensors may be used that include a sensor for reading the measurement spot, a sensor for detecting the position of the starting point of the analyzing device, and a sensor for detecting the trigger mark. Alternatively, a sensor can be shared by arranging the starting point and the trigger mark of the analyzing device on the same circumference with completely different shapes. In this case, however, signal processing is necessary for detecting the different shapes in real time during a rotation of the analyzing device. Further, instead of the provision of the trigger mark, a rotary encoder may be attached to a turntable. In the case of a small analyzing device, a high resolution is necessary. In these methods, however, the measurement spot is read and the position of the measurement spot is detected by different sensors. Therefore, the detected position of the measurement spot may be displaced by the installation errors of the sensors or a fitting gap between the analyzing device and the turntable.

The present invention has been devised to solve the problem of the prior art. An object of the present invention is to provide an analyzing apparatus and a position detecting method that can achieve reliable reading without increasing the number of sensors or the number of components for detecting a position.

Means for Solving the Problem

An analyzing apparatus of the present invention includes: an analyzing device having a microchannel structure for transferring a sample liquid to a measurement spot by a centrifugal force; a rotating unit for rotating the set analyzing device; a light source and a photodetector opposed to each other with the set analyzing device disposed between the light source and the photodetector; and a reading device for detecting output light having passed through the measurement spot of the analyzing device, by using the photodetector, the analyzing device including position detection marks, each having one of a reflective surface, a refractive surface, and a light shielding surface that block the output light incident on the photodetector from the light source when the output light reaches a rotation detection position just before or behind the measurement spot, the reading device including a signal processor that extracts the output light just having passed through the measurement spot of the analyzing device and calculates a component of the sample liquid based on the rotation detection signal of the analyzing device and the detection signal of the photodetector, the rotation detection signal being obtained from the rotating unit.

The analyzing device has a starting point position mark indicating the position of a starting point in the direction of rotation, in addition to the position detection mark, and the signal processor extracts a signal at a predetermined time out of the analyzing signals and calculates the component of the sample liquid based on the starting point position mark, the rotation detection signal, and the position reading signal of the position detection mark.

The position detection marks are provided upstream and downstream of the measurement spot in the direction of rotation, and the signal processor extracts the analyzing signal read between the first position detection mark and the second position detection mark when the trigger width of the first position detection mark, the trigger width of the second position detection mark, and an interval between the first position detection mark and the second position detection mark are within a permissible range.

The position detection mark is provided on one of the upstream side and the downstream side of the measurement spot in the direction of rotation, and the signal processor determines the position of the measurement spot based on the trigger width of the position detection mark and the rotation detection signal and extracts the analyzing signal.

A position detecting method of the analyzing apparatus according to the present invention, the analyzing apparatus including: an analyzing device having a microchannel structure for transferring a sample liquid to a measurement spot by a centrifugal force; a rotating unit for rotating the set analyzing device; a light source and a photodetector opposed to each other with the set analyzing device disposed between the light source and the photodetector; and a reading device for detecting output light having passed through the measurement spot of the analyzing device, by using the photodetector, the analyzing device including position detection marks, each having one of a reflective surface, a refractive surface, and a light shielding surface that block the output light incident on the photodetector from the light source when the output light reaches a rotation detection position just before or behind the measurement spot, the reading device including a signal processor that extracts the output light just having passed through the measurement spot of the analyzing device and calculates a component of the sample liquid based on the rotation detection signal of the analyzing device and the detection signal of the photodetector, the rotation detection signal being obtained from the rotating unit, the method including: rotating the analyzing device by using the rotating unit; counting the rotation detection signals from the starting point position mark; turning on the light source when the number of rotation detection signals reaches a predetermined number; detecting the output light having passed through the analyzing device, by using the photodetector; turning off the light source a predetermined time after the light source is turned on or when the number of rotation detection signals reaches the predetermined number; extracting the position detection mark from the detected signal; and specifying the position of the measurement spot based on the extracted position detection mark and information about the positional relationship between the stored position detection mark and the measurement spot.

Further, the position of the measurement spot is specified based on the extracted position detection mark, the number of revolutions of the analyzing device, and the information about the positional relationship between the stored position detection mark and the measurement spot, the number of revolutions being obtained from the rotation detection signal.

Advantage of the Invention

According to this configuration, a reading device is configured such that output light having passed through the measurement spot of an analyzing device is detected by a photodetector, and the analyzing device includes a position detection mark having one of a reflective surface, a refractive surface, and a light shielding surface that block the output light incident on the photodetector from a light source when the output light reaches a rotation detection position just before or behind the measurement spot. Thus it is possible to determine the position of the measurement spot based on the output signal of a sensor for reading the measurement spot and properly extract a desired analyzing signal.

BEST MODE FOR CARRYING OUT THE INVENTION

Referring to FIGS. 1 to 13, the following will describe embodiments of an analyzing apparatus according to the present invention.

First Embodiment

FIGS. 1 to 9A, 9B, 9C, 9D, and 13 show a first embodiment of the present invention.

FIGS. 7A, 7B to 9A, 9B, 9C, and 9D show an analyzing device.

Figure 7A:
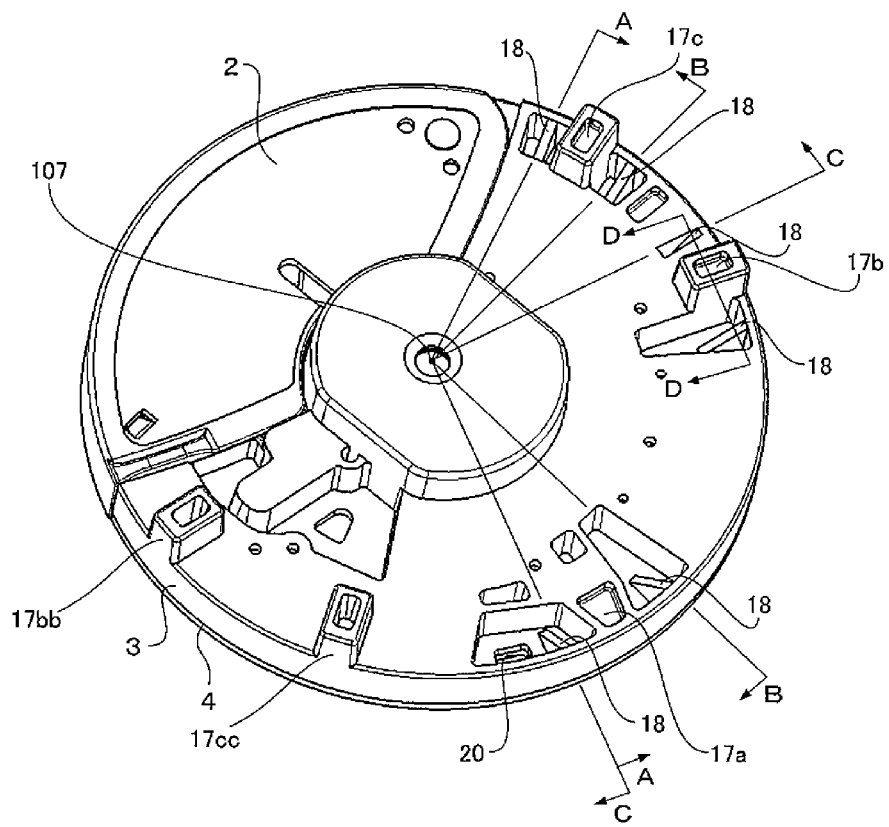
FIG. 7A is an outside perspective view showing the analyzing device with a closed protective cap according to the first embodiment.
Figure 7B:
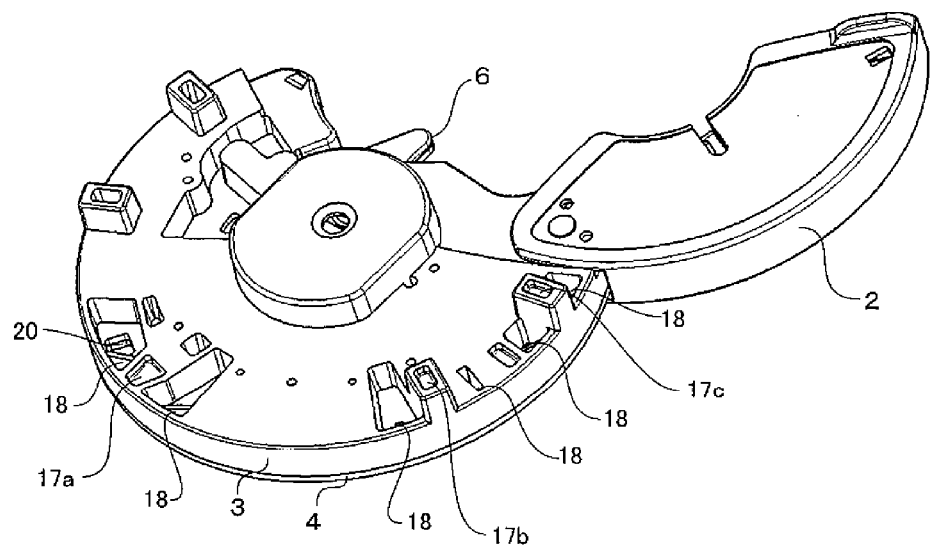
FIG. 7B is an outside perspective view showing the analyzing device with an opened protective cap according to the first embodiment.
Figure 8:
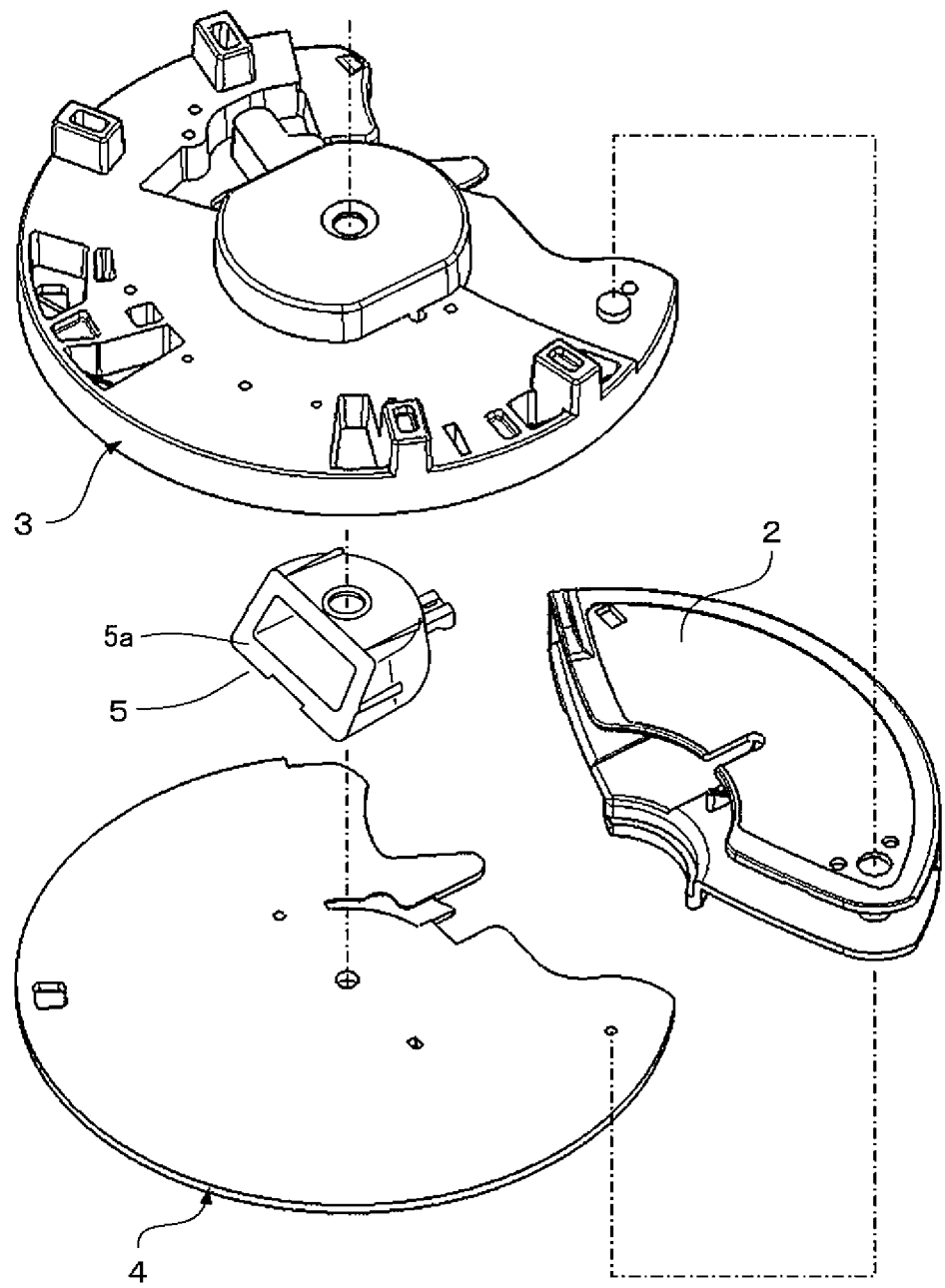
FIG. 8 is an exploded perspective view showing the analyzing device according to the first embodiment.
Figure 9A:
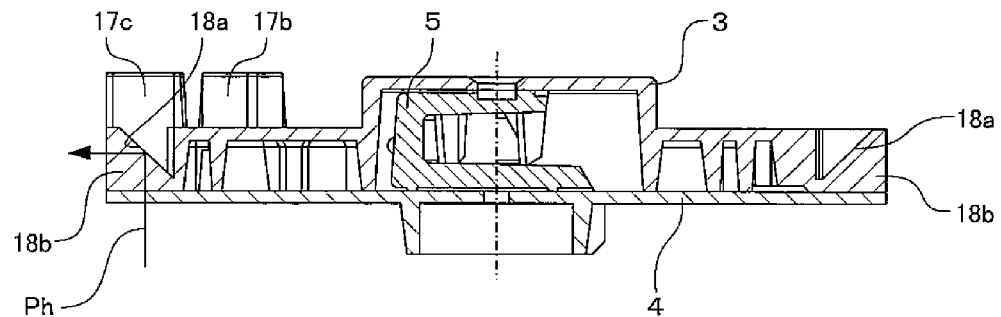
FIG. 9A is a sectional view taken along line A-A of FIG. 7A of the first embodiment.
Figure 9B:
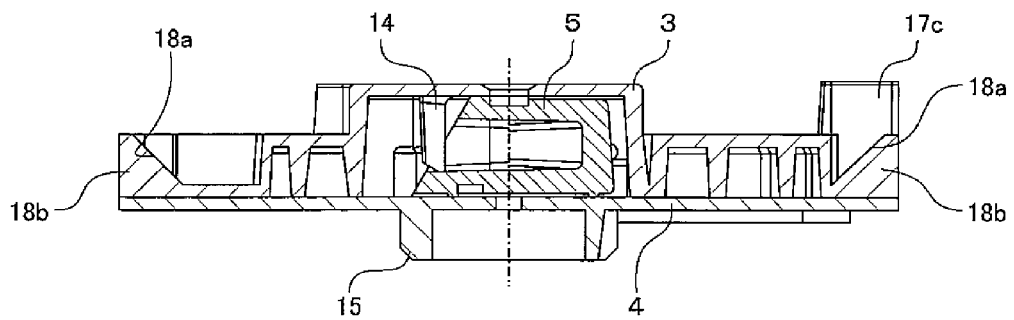
FIG. 9B is a sectional view taken along line B-B of FIG. 7A of the first embodiment.
Figure 9C:
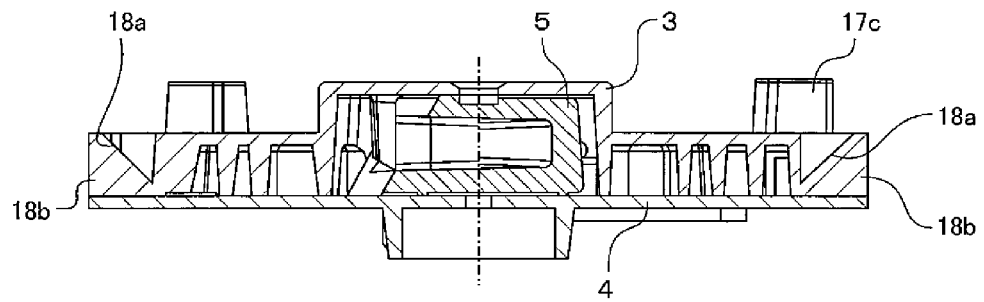
FIG. 9C is a sectional view taken along line C-C of FIG. 7A of the first embodiment.
Figure 9D:
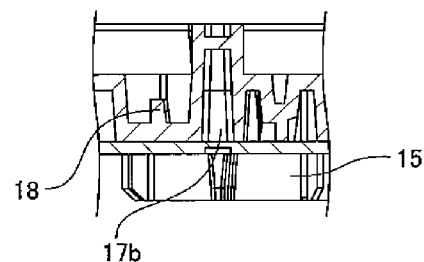
FIG. 9D is a sectional view taken along line D-D of FIG. 7A of the first embodiment.

FIGS. 7A and 7B show an analyzing device 1 with an opened and closed protective cap 2. FIG. 8 is an exploded view of the analyzing device 1 with the underside of FIG. 7A placed face up. FIG. 9A is a sectional view taken along line A-A of FIG. 7A. FIG. 9B is a sectional view taken along line B-B of FIG. 7A. FIG. 9C is a sectional view taken along line C-C of FIG. 7A. FIG. 9D is a sectional view taken along line D-D of FIG. 7A.

The analyzing device 1 shown in FIGS. 7A, 7B, and 8 is made up of four components of a base substrate 3 having a microchannel structure formed on one surface, the microchannel structure having a minutely uneven surface, a cover substrate 4 for covering the surface of the base substrate 3, a diluent container 5 for retaining a diluent, and the protective cap 2 for preventing splashes of a sample liquid.

The base substrate 3 and the cover substrate 4 are joined to each other with the diluent container 5 and so on set in the base substrate 3 and the cover substrate 4, and the protective cap 2 is attached to the joined base substrate 3 and cover substrate 4. An opening 5a of the diluent container 5 is sealed with aluminum foil (not shown) after the diluent is applied into the diluent container 5.

The cover substrate 4 covers the openings of several recessed portions formed on the top surface of the base substrate 3, thereby forming multiple measurement spots 17a, 17b, and 17c, the passages of the microchannel structure connecting the measurement spots, and so on.

The outline of an analyzing process using the analyzing device 1 is that a sample liquid is dropped into an inlet 6 of the analyzing device 1 in which the diluent has been set, the diluent container 5 is moved by closing the protective cap 2 and the aluminum foil in the opening 5a is broken by a protrusion 14 as shown in FIG. 9B, so that the diluent starts flowing. The flowing sample liquid is measured after being diluted with the diluent.

Figure 4:
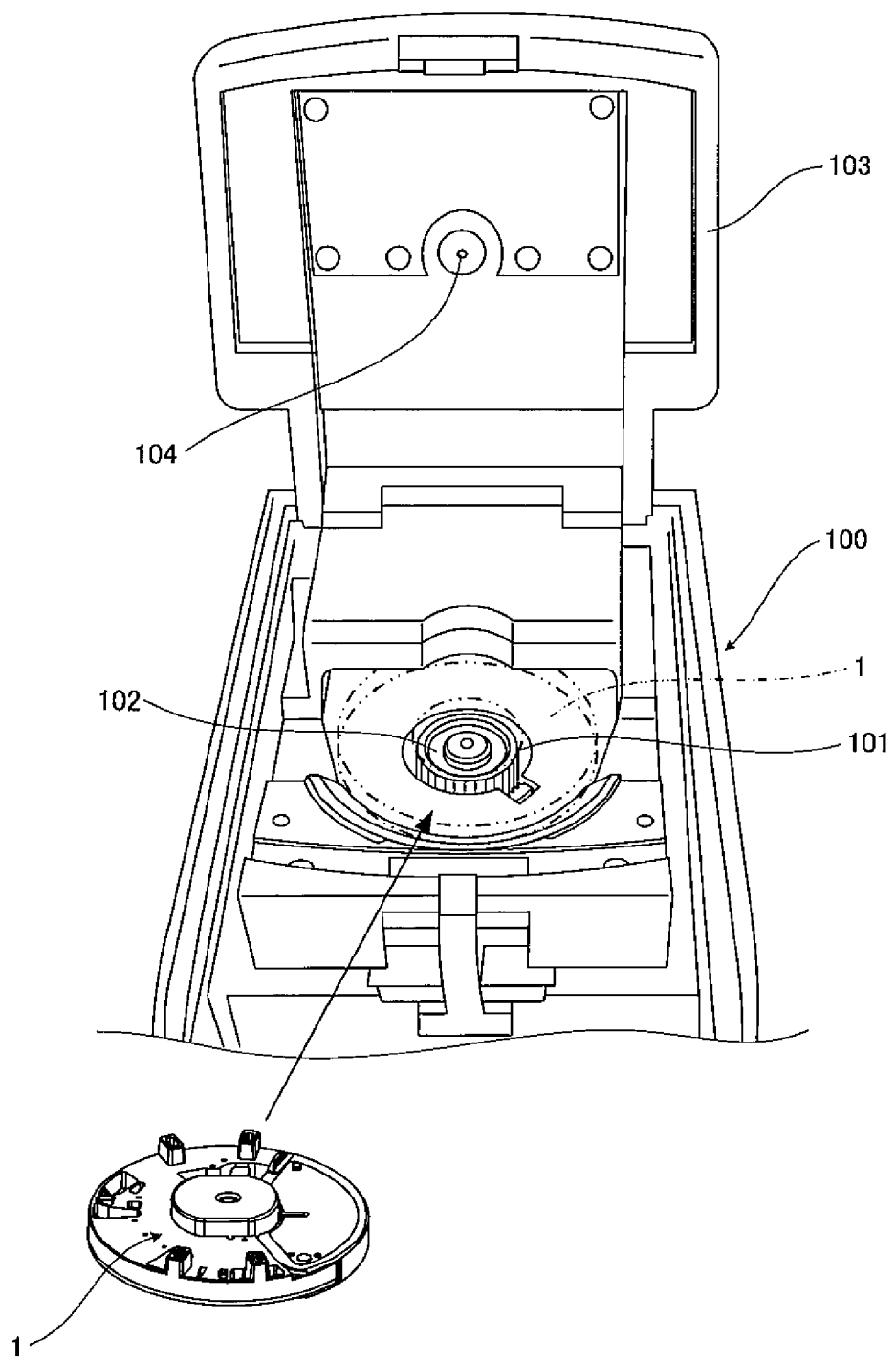
FIG. 4 is a perspective view showing the analyzing apparatus with an opened door according to the first embodiment.
Figure 5:
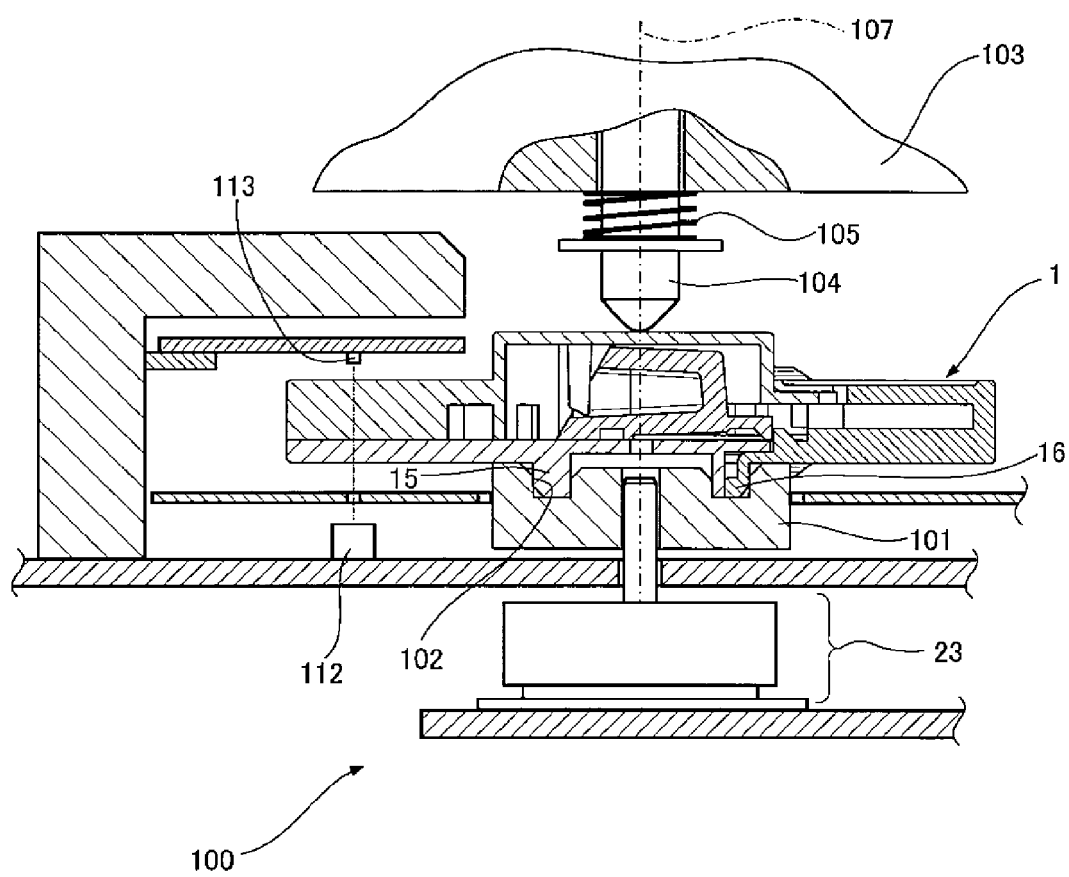
FIG. 5 is a sectional view showing the principle part of the analyzing apparatus with the analyzing device set in the analyzing apparatus.

FIG. 4 shows that a door 103 of an analyzing apparatus 100 is opened. FIG. 5 shows that the analyzing device 1 is set on a turntable 101 and the door 103 is closed.

On the top surface of the turntable 101 of the analyzing apparatus 100, a groove 102 is formed. In a state in which the analyzing device 1 is set on the turntable 101, rotary support parts 15 and 16 formed on the cover substrate 4 and the protective cap 2 of the analyzing device 1 are engaged with the groove 102, so that the analyzing device 1 is accommodated.

After the analyzing device 1 is set on the turntable 101, the door 103 of the analyzing apparatus is closed before a rotation of the turntable 101, so that the set analyzing device 1 is pressed to the turntable 101 by a movable piece 104 provided on the door 103, by a biasing force of a spring 105 at a position on the rotation axis of the turntable 101. Thus the analyzing device 1 rotates together with the turntable 101 that is rotationally driven by a rotating unit 106. Reference numeral 107 denotes the axis of rotation of the turntable 101.

Figure 6:
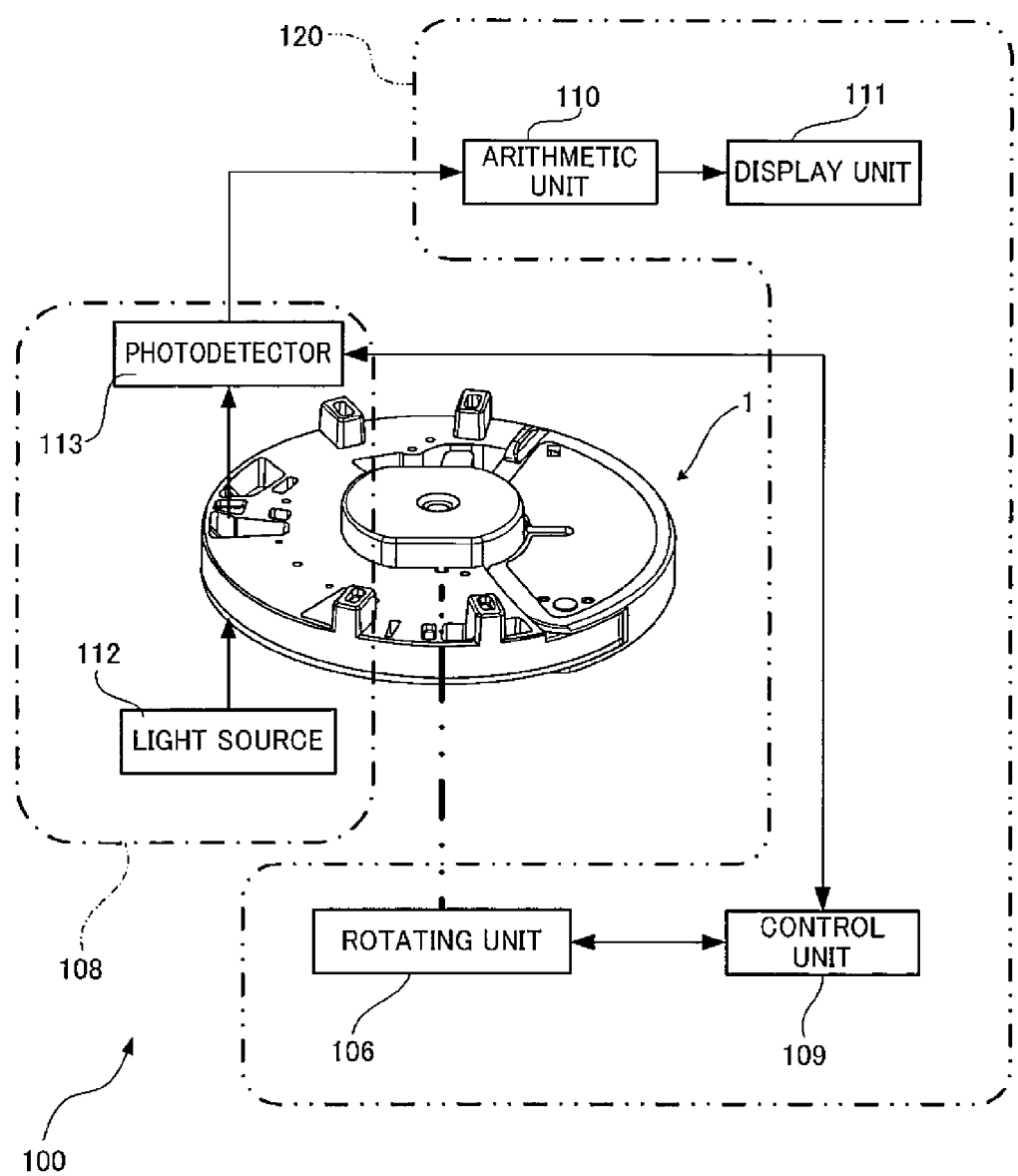
FIG. 6 is a block diagram showing the analyzing apparatus according to the first embodiment.

FIG. 6 shows the configuration of the analyzing apparatus 100.

The analyzing apparatus 100 is made up of the rotating unit 106 for rotating the turntable 101; an optical measuring unit 108 for optically measuring a solution in the analyzing device 1; a control unit 109 for controlling the rotation speed and rotation direction of the turntable 101, the measurement timing of the optical measuring unit, and so on; an arithmetic unit 110 for calculating a measurement result by processing a signal obtained by the optical measuring unit 108; and a display unit 111 for displaying the result obtained by the arithmetic unit 110.

The rotating unit 106 can rotate the analyzing device 1 through the turntable 101 about the rotation axis 107 in any direction at a predetermined rotation speed and can further vibrate the analyzing device 1 so as to laterally reciprocate the analyzing device 1 at a predetermined stop position with respect to the rotation axis 107 with a predetermined amplitude range and a predetermined period.

The optical measuring unit 108 includes a light source 112 for emitting detection light to a measurement spot of the analyzing device 1; and a photodetector 113 for detecting an amount of light having passed through the analyzing device 1 as a reading device for accessing the measurement spot and reading a signal.

The analyzing device 1 is rotationally driven by the turntable 101, and the sample liquid drawn into the analyzing device 1 from the inlet 6 is transferred in the analyzing device 1 by a centrifugal force generated by rotating the analyzing device 1 about the rotation axis 107 located inside the inlet 6 and the capillary force of a capillary passage provided in the analyzing device 1.

Figure 1:
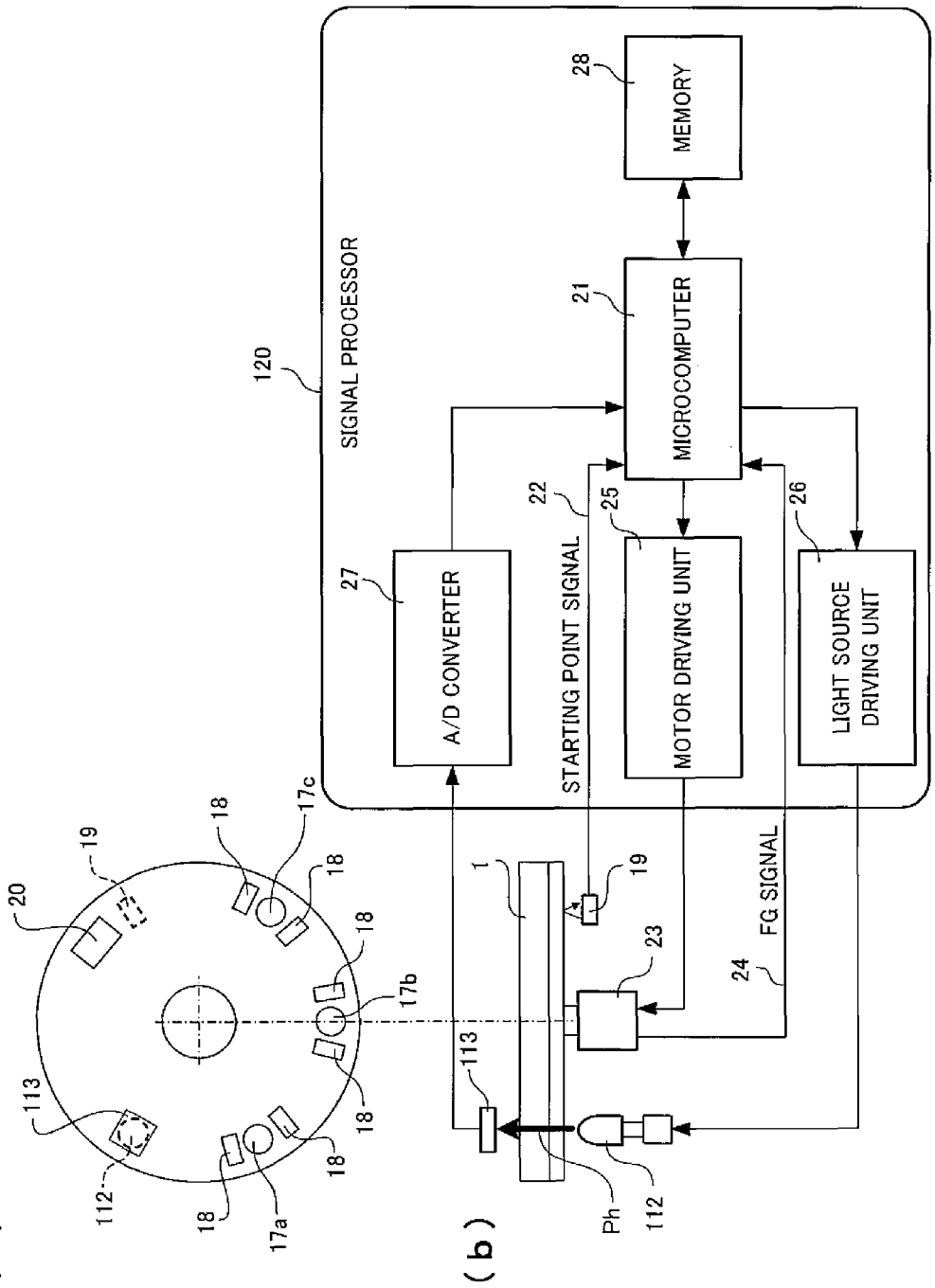
FIG. 1 shows a schematic plan view of an analyzing device and a part around the analyzing device in an analyzing apparatus and a structural diagram of a signal processor according to a first embodiment of the present invention.
Figure 2:
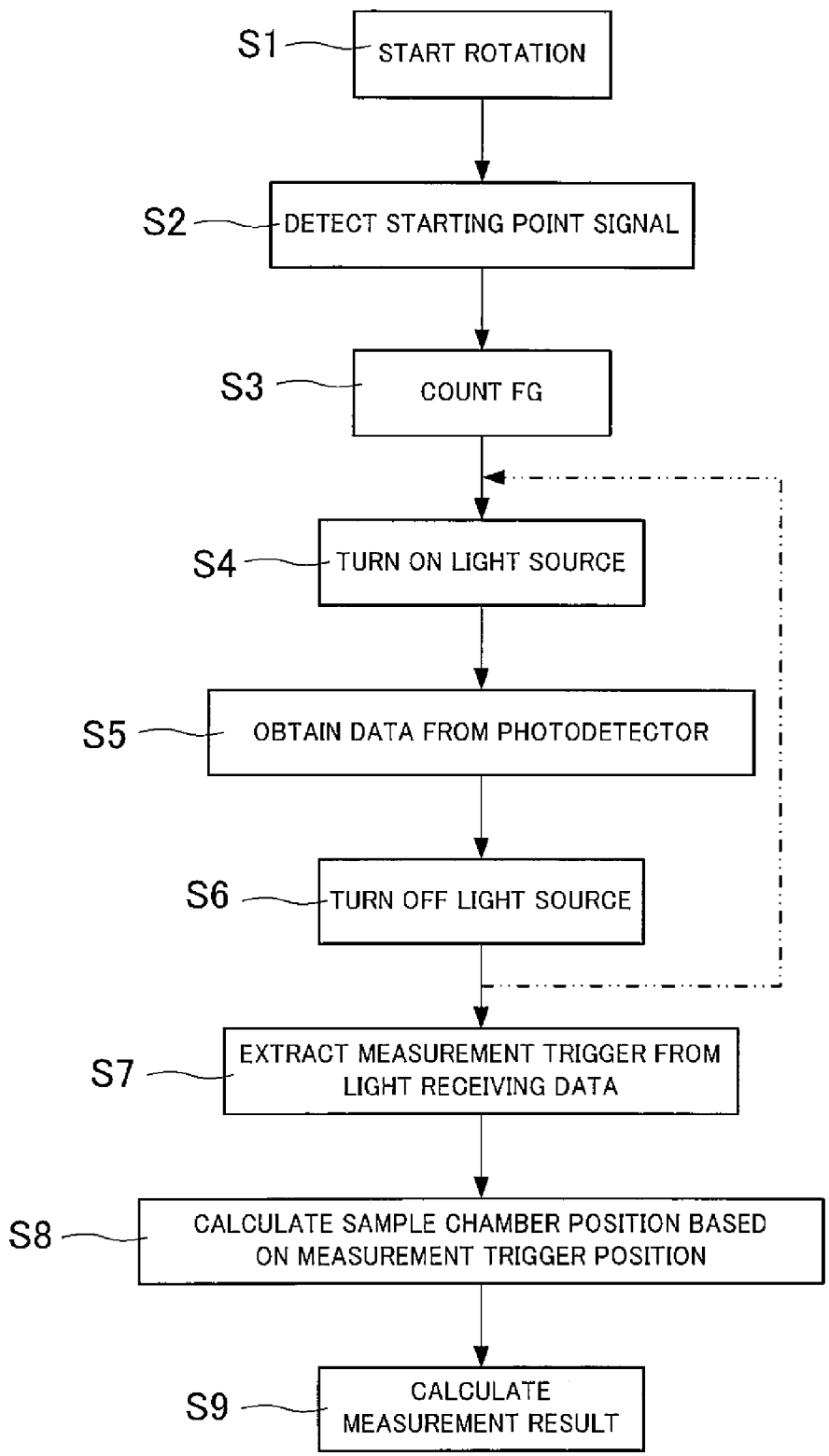
FIG. 2 is a flowchart of a microcomputer according to the first embodiment.
Figure 3:
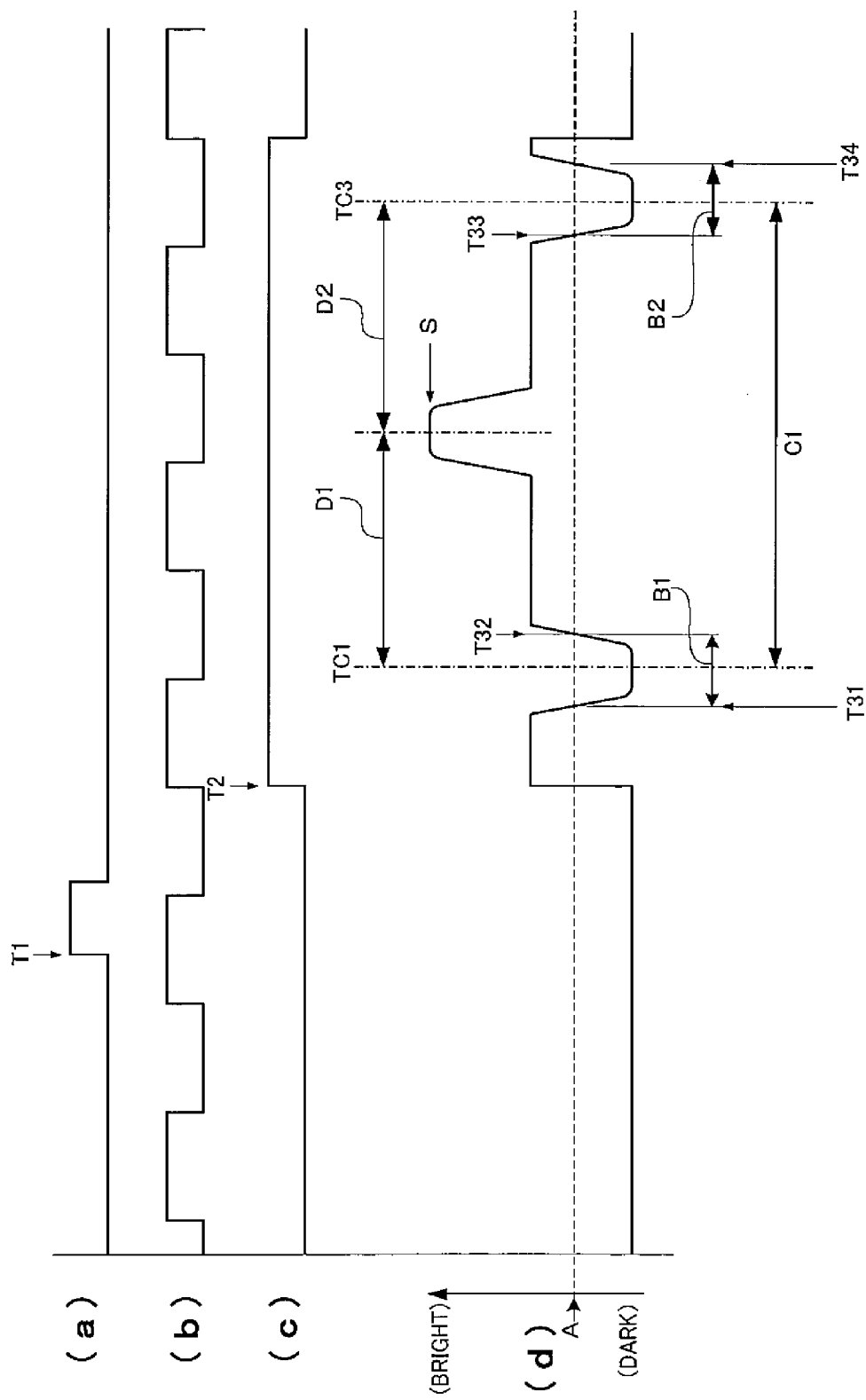
FIG. 3 is a timing chart of the first embodiment.

FIGS. 1 to 3 show a signal processor 120 in which the rotating unit 106, the control unit 109, the arithmetic unit 110, and the display unit 111 in FIG. 6 are realized by a microcomputer.

In the analyzing device 1 of the analyzing apparatus 100, the first to third measurement spots 17a, 17b, and 17c are formed at the same radius of the analyzing device 1. On the upstream and downstream sides of the first to third measurement spots 17a, 17b, and 17c, position detection marks 18 are provided. As shown in FIGS. 9A, 9B, and 9C, the position detection mark 18 is made up of a rib 18b having an inclined surface 18a on which detection light Ph from the light source 112 is totally reflected to the outer periphery of the analyzing device 1, so that the detection light Ph is not incident on the photodetector 113.

In FIG. 7A, protrusions 17bb and 17cc that are symmetric about the measurement spots 17b and 17c with respect to the axis 107 are formed on the base substrate 3 as balance weights for balancing the rotation of the analyzing device 1.

The analyzing apparatus 100 is provided with a starting point sensor 19 for detecting the absolute position of the set analyzing device 1. The starting point sensor 19 outputs a starting point signal 22 to a microcomputer 21 at the detection of a starting point position mark 20 of a through hole formed on the analyzing device 1 as shown in FIGS. 7A and 7B.

In FIGS. 1 and 5, a brushless motor 23 for rotationally driving the turntable 101 has a plurality of stator coils, an outer rotor, a magnet diode that is provided on a stator and detects a magnetized state of the outer rotor passing in front of the stator, and an energization switching part that rotationally drives the outer rotor by switching energization to the plurality of stator coils based on the detection of the magnet diode. From the output of the magnet diode, an FG signal 24 (see FIG. 3(b)) is obtained in synchronization with a rotation of the outer rotor. To be specific, the period of the FG signal is inversely proportional to the rotation speed of the outer rotor.

Figure 13:
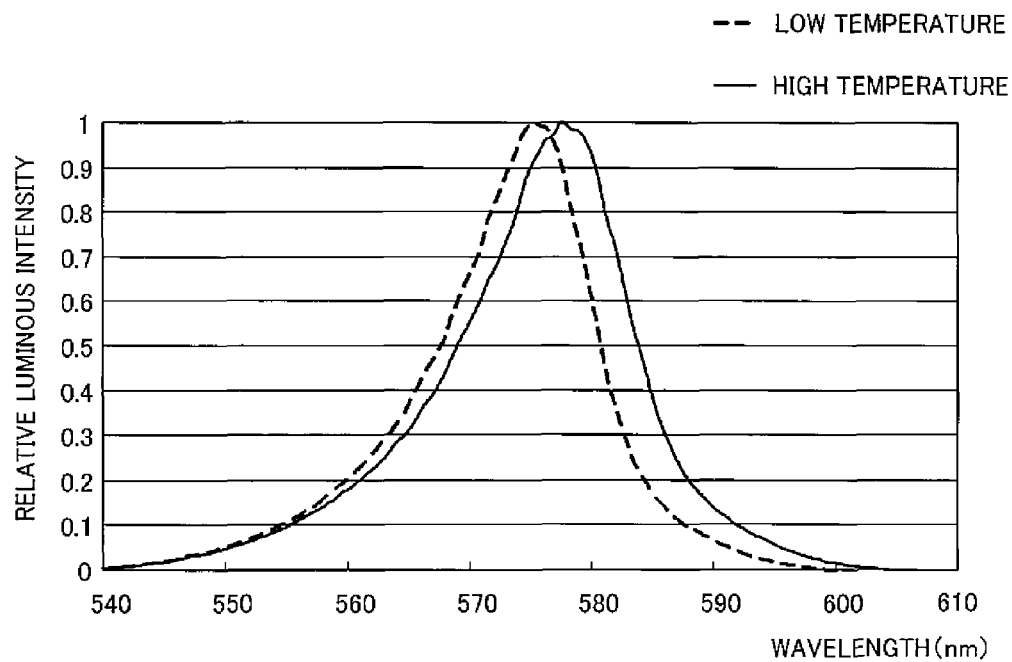
FIG. 13 is a spectrum diagram showing a light emitting diode acting as a light source of the first embodiment.
Figure 14:
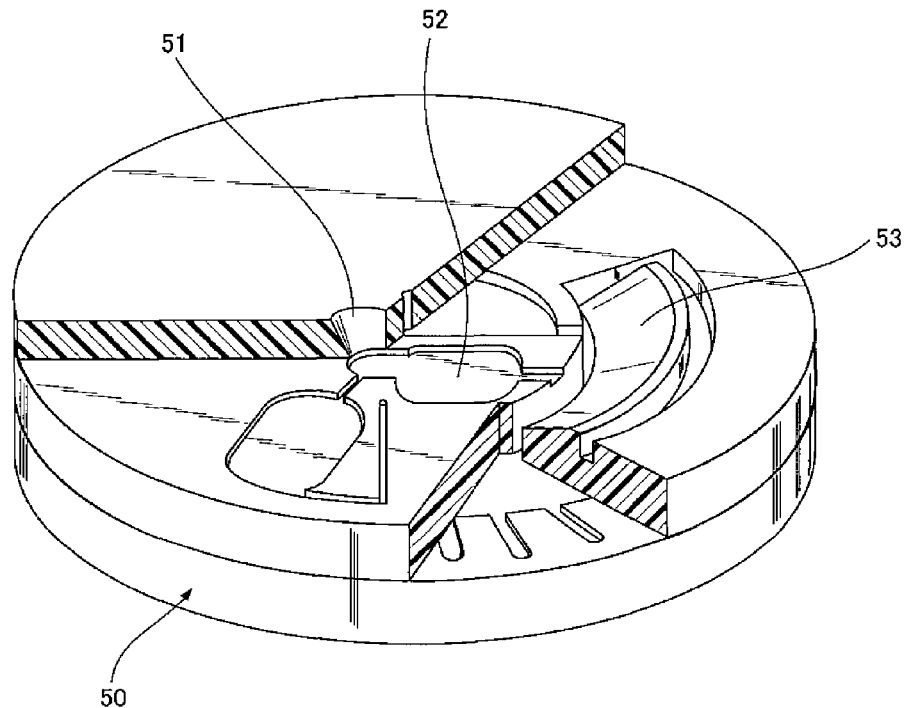
FIG. 14 is a partially cut perspective view showing an analyzing device of Patent Document 1.

FIG. 13 shows a wavelength spectrum of a light emitting diode.

Light emitting diodes have been recently used as various light sources because of its long life, low power consumption, small size, and low cost. In FIG. 13, a broken line indicates a wavelength spectrum at low temperature and a solid line indicates a wavelength spectrum at high temperature. When a light emitting diode is used as a light source for measurement, the wavelength spectrum varies with temperature. Thus even when the concentration of a sample and a spectrum absorbed by the sample do not change, an amount of light received by the photodetector 113 fluctuates. In other words, when the light source 112 is a light emitting diode, heat generated by the light emission of the light source 112 continuously turned on results in a temperature rise of the light emitting diode and changes the wavelength. Hence it is necessary to control light in a pulsing manner so as to suppress the heat of the light emitting diode.

FIG. 2 shows the configuration of the microcomputer 21.

In step S1, the microcomputer 21 instructs the brushless motor 23 to start a rotation through a motor driving unit 25.

In step S2, the generation of the starting point signal 22 is detected (at time T1 of FIG. 3(a)). In step S3, the counting of the FG signal 24 is started in response to the detection. In step S4, when it is detected that the count of the FG signals 24 reaches a predetermined value, the light source 112 is turned on through a light source driving unit 26 (at time T2 of FIG. 3(c)).

The light source 112 is turned on, the rib 18b upstream of the first measurement spot 17a passes in front of the photodetector 113, the first measurement spot 17a passes in front of the photodetector 113, and the rib 18b downstream of the first measurement spot 17a passes in front of the photodetector 113, so that in step S5, the detection signal of the photodetector 113 is captured through an A/D converter (analog/digital converter) 27 as shown in FIG. 3(d). Data of FIG. 3(d) is recorded in a memory 28 so as to correspond to the sequential counts of the FG signals 24 that have been counted from step S3.

In step S6, the light source 112 is turned off when it is detected that a predetermined time has elapsed or the count of the FG signals 24 reaches the predetermined value.

Actually, also on the second measurement spot 17b and the third measurement spot 17c, steps S4 to S6 are repeated as on the first measurement spot 17a, and data is collected in the memory 28 until data of the second and third measurement spots 17b and 17c has been collected. In this example, signal processing on the first measurement spot 17a will be described.

In step S7, time T31 is specified where the level of the photodetector 113 falls below a threshold value A immediately after the starting point signal 22 as shown in FIG. 3(b). Further, time T32 is specified where the level of the photodetector 113 exceeds the threshold value A immediately after the starting point signal 22, and it is determined whether or not an interval B1 between time T31 and time T32 reaches a known width of the first rib 18b based on the FG signal 24.

Next, time T33 is specified where the level of the photodetector 113 falls below the threshold value A. Further, time T34 is specified where the level of the photodetector 113 exceeds the threshold value A, and it is determined whether or not an interval B2 between time T33 and time T34 reaches a known width of the second rib 18b based on the FG signal 24.

When the interval reaches the known width of the first rib 18b and the known width of the second rib 18b, it is determined whether or not an interval C1 between a center TC1 of time T31 and time T32 and a center TC3 of time T33 and T34 reaches a known interval between the first and second ribs 18b. In the case where this condition is satisfied, in step S8, the position of the first measurement spot 17a is determined based on a distance D1 from the center TC1 of time T31 and time T32 to the first center of the first measurement spot 17a or a distance D2 from the center TC3 of time T33 and time T34 to the center of the first measurement spot 17a. The distances D1 and D2 are determined based on the interval C1 and the relative positions (ratio) of the first and second ribs 18b and the first measurement spot 17a, the relative positions being specified by the physical layout of the analyzing device 1. In step S9, a detected value S of the photodetector 113 is read from the collected data of the memory 28 based on the determined position, and a component amount is calculated based on the amount of transmitted light.

When the condition is not satisfied in step S8, a program is run to repeat steps S2 to S8 a predetermined number of times on the first measurement spot 17a. In the case where the condition is not satisfied even after the number of repetitions reaches the upper limit, a measurement error is outputted for the first measurement spot 17a.

The same processing is performed on the second and third measurement spots 17b and 17c as on the first measurement spot 17a.

Since the ribs 18b are provided as the position detection marks 18 on the analyzing device, it is possible to detect positions just before and behind the measurement spot by using a sensor for reading the measurement spot, thereby properly extracting a desired analyzing signal.

Moreover, the position of the measurement spot is roughly estimated by counting the FG signals 24 and is exactly calculated by analyzing data containing the position detection mark 18. Thus it is possible to obtain a relatively satisfactory measurement result without adding a position detecting component such as a rotary encoder having high resolution.

Second Embodiment

Figure 10:
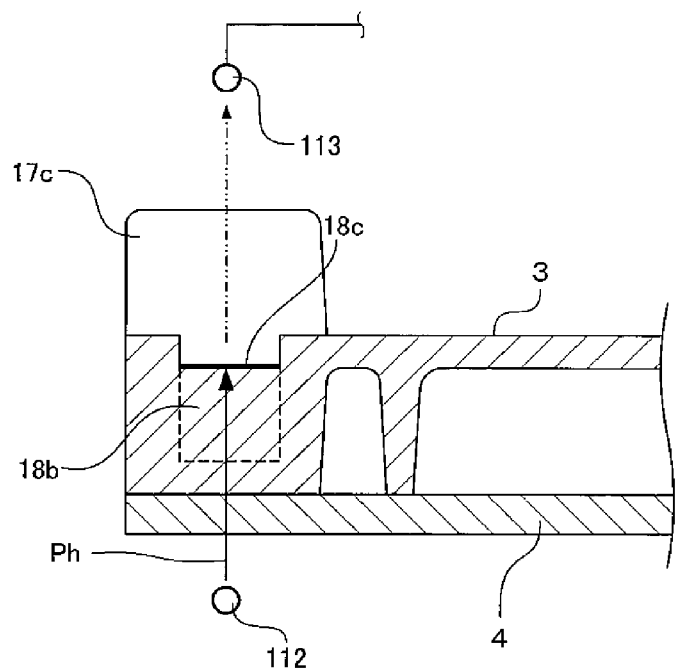
FIG. 10 is a sectional view showing the principle part of an analyzing device according to a second embodiment.

FIG. 10 shows a second embodiment of the present invention.

In the first embodiment, the rib 18b having the inclined surface 18a is provided as the position detection mark 18 on the analyzing device, and the inclined surface 18a acting as a reflective surface blocks output light that is incident on the photodetector 113 from the light source 112 when the output light reaches rotation detection positions just before and behind the measurement spot. In the second embodiment, as shown in FIG. 10, a rib 18b has a different shape and a light shielding membrane 18c through which light is hardly transmitted is formed on the end face of the rib 18b.

Also in this configuration, the parts of a signal processor 120 are fed with the same input signals as in FIG. 3. Thus it is possible to detect positions just before and behind a measurement spot by using a sensor for reading the measurement spot, thereby properly extracting a desired analyzing signal.

Third Embodiment

Figure 11:
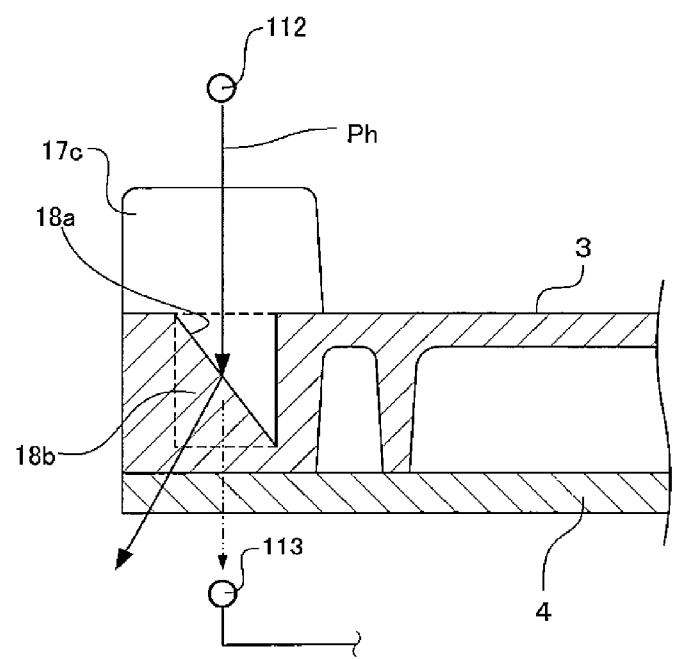
FIG. 11 is a sectional view showing the principle part of an analyzing device according to a third embodiment.

FIG. 11 shows a third embodiment of the present invention.

In the first embodiment, the inclined surface 18a acts as a reflective surface such that the detection light Ph emitted from the light source 112 is not incident on the photodetector 113. As shown in FIG. 11, when detection light Ph emitted from a light source 112 is incident on a rib 18b from a base substrate 3, an inclined surface 18a acts as a refractive surface and the detection light Ph emitted from the light source 112 is not incident on a photodetector 113 at a position detection mark 18. Other points are similar to those of the first embodiment.

Fourth Embodiment

Figure 12:
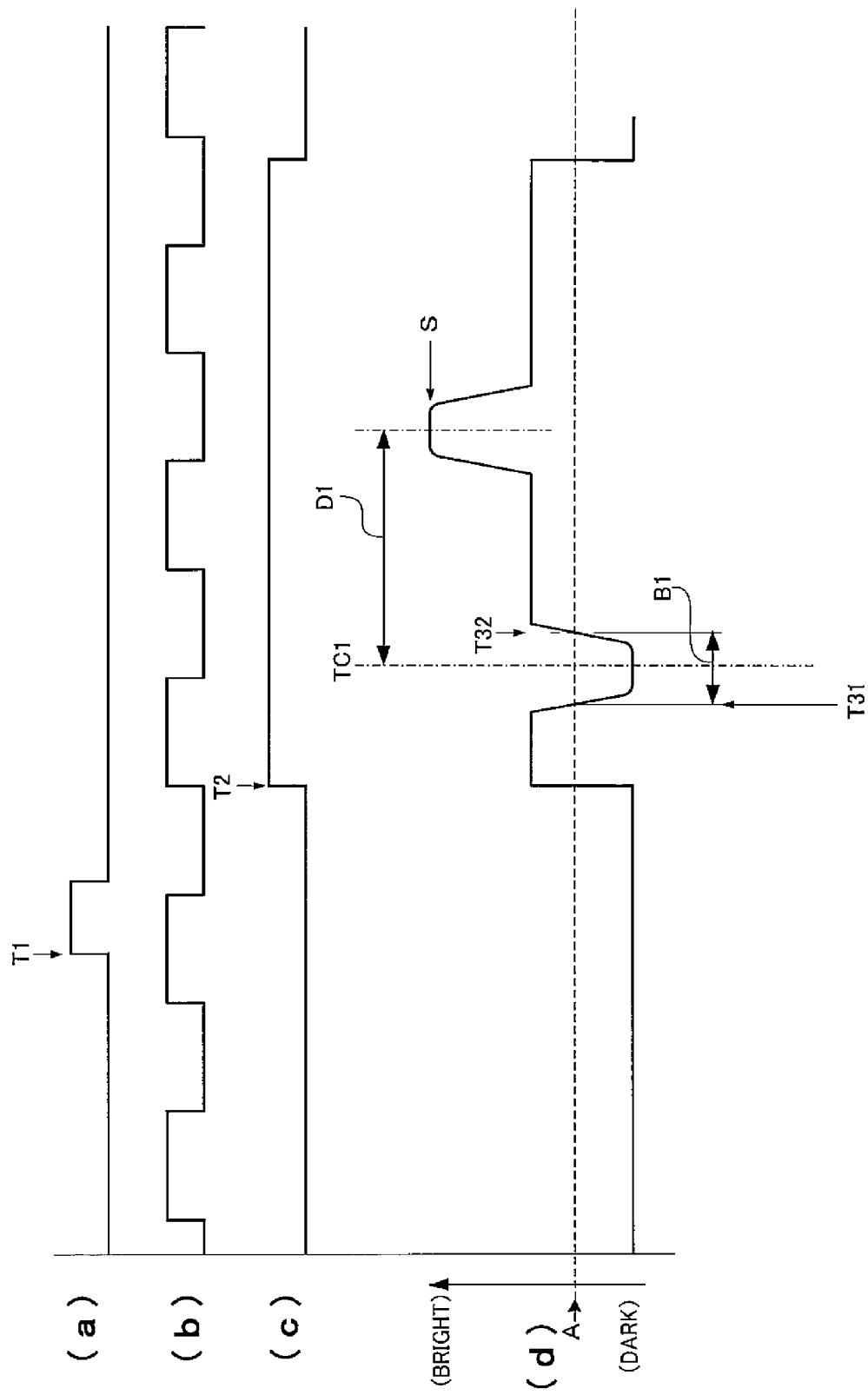
FIG. 12 is a timing chart of a fourth embodiment.

FIG. 12 shows a fourth embodiment of the present invention.

In the foregoing embodiments, the position detection marks 18 are provided upstream and downstream of the measurement spot in a direction of rotation, and the signal processor 120 is configured such that when the trigger width B1 of the upstream position detection mark 18, the trigger width B2 of the downstream position detection mark 18, and the interval C1 between the upstream position detection mark 18 and the downstream position detection mark 18 are within a permissible range, the analyzing signal read between the upstream position detection mark 18 and the downstream position detection mark 18 is extracted from the analyzing signals written in the memory 28. In the fourth embodiment, a position detection mark 18 is provided only one of the upstream side and the downstream side of a measurement spot. Also in this case, it is possible to extract desired one of the analyzing signals written in a memory 28.

FIG. 12 shows an input signal of a signal processor 120 when the position detection mark 18 is provided only on the upstream side of the measurement spot. In this case, in the signal processor 120, the actual number of revolutions of an analyzing device is measured at the acquisition of light receiving data and the light receiving data is binarized by a threshold value A. After that, it is confirmed whether a width B1 of the light receiving data of the position detection mark 18 is not larger than a predetermined value. The time when the width B1 of the light receiving data is not larger than the predetermined value is recognized as the position detection mark 18. Relative to a distance D1 (a distance from the center of the position detection mark to the center of the measurement spot) to a measurement spot determined beforehand based on the physical layout of the analyzing device, a specified number of revolutions, and the sampling speed of an A/D converter 27, a distance of the light receiving data written in the memory 28 is recalculated using an actual number of revolutions of the analyzing device when the light receiving data is actually obtained. Thus the position of the measurement spot is determined and necessary light receiving data is extracted. The following is a specific calculation example.

Assuming that the center of the position detection mark 18 and the center of the measurement spot forms an angle of 36°, the specified number of revolutions is 1500 rpm, and the A/D converter 27 has a sampling speed of 1 MSPS, the distance D1 is expressed as follows:

((60[seconds]÷1500 [rpm]×3.6 [deg])/360 [deg])×1 M [Sample]=400 [Sample]

Assuming that the actual number of revolutions of the analyzing device is 2000 rpm at the acquisition of the light receiving data, the actual measurement spot distance D1 having been stored in the signal processor 120 is expressed as follows:

400 [Sample]×1500 [rpm]÷2000 [rpm]=300 [Sample]

INDUSTRIAL APPLICABILITY

The present invention makes it possible to perform mixing and agitation in a short time in an analyzing device used for analyzing a component of a liquid collected from an organism and the like, keep the analysis accuracy, and improve the analysis efficiency.

The invention claimed is:

1. A position detecting method of an analyzing apparatus comprising: an analyzing device having a microchannel structure for transferring a sample liquid to a measurement spot by a centrifugal force; a rotating unit for rotating the set analyzing device; a light source and a photodetector opposed to each other with the set analyzing device disposed between the light source and the photodetector; and a reading device for detecting output light having passed through the measurement spot of the analyzing device, by using the photodetector, the analyzing device including position detection marks, each having one of a reflective surface, a refractive surface, and a light shielding surface that block the output light incident on the photodetector from the light source when the output light reaches a rotation detection position just before or behind the measurement spot, the reading device including a signal processor that extracts the output light just having passed through the measurement spot of the analyzing device and calculates a component of the sample liquid based on a rotation detection signal of the analyzing device and a detection signal of the photodetector, the rotation detection signal being obtained from the rotating unit, the method comprising: rotating the analyzing device by using the rotating unit; counting the rotation detection signals from the starting point position mark; turning on the light source when a number of rotation detection signals reaches a predetermined number; detecting the output light having passed through the analyzing device, by using the photodetector; turning off the light source a predetermined time after the light source is turned on or when the number of rotation detection signals reaches the predetermined number; extracting the position detection mark from the detected signal; and specifying a position of the measurement spot based on the extracted position detection mark and information about a positional relationship between the stored position detection mark and the measurement spot.

2. The position detecting method of an analyzing apparatus according to claim 1, wherein the position of the measurement spot is specified based on the extracted position detection mark, a number of revolutions of the analyzing device, and the information about the positional relationship between the stored position detection mark and the measurement spot, the number of revolutions being obtained from the rotation detection signal.

* * * * *